(12) United States Patent
Koenig et al.

(10) Patent No.: US 7,485,110 B2
(45) Date of Patent: Feb. 3, 2009

(54) WIPE COMPRISING A PATHOGEN SELECTIVE ANTIMICROBIAL

(75) Inventors: David W. Koenig, Menasha, WI (US); Lisa Marie Kroll, Appleton, WI (US)

(73) Assignee: Kimberly Clark Worldwide, Inc.

( * ) Notice: Subject to any disclaimer, the term of this patent is extended or adjusted under 35 U.S.C. 154(b) by 776 days.

(21) Appl. No.: 10/608,661

(22) Filed: Jun. 27, 2003

(65) Prior Publication Data

US 2004/0039353 A1 Feb. 26, 2004

Related U.S. Application Data

(63) Continuation-in-part of application No. 10/029,404, filed on Dec. 20, 2001, now Pat. No. 6,891,079.

(51) Int. Cl.
*A61M 35/00* (2006.01)
*A01N 65/00* (2006.01)
*A61K 36/00* (2006.01)
*A61K 36/82* (2006.01)

(52) U.S. Cl. .............. 604/289; 604/290; 424/725; 424/729; 424/776

(58) Field of Classification Search .......... 604/290, 604/360; 510/130; 424/401, 402, 404
See application file for complete search history.

(56) References Cited

U.S. PATENT DOCUMENTS

| | | | |
|---|---|---|---|
| 4,100,324 A | 7/1978 | Anderson et al. |
| 4,167,559 A | 9/1979 | Michel |
| 4,623,339 A | 11/1986 | Ciraldo et al. |
| 4,657,766 A | 4/1987 | Goodall |
| 4,772,479 A | 9/1988 | Goodall |
| 4,798,603 A | 1/1989 | Meyer et al. |
| 4,828,860 A | 5/1989 | Goodall |
| 5,017,562 A | 5/1991 | Holmes et al. |
| 5,110,593 A | 5/1992 | Benford |
| 5,139,779 A | 8/1992 | McNeff |
| 5,176,668 A | 1/1993 | Bernardin |
| 5,176,672 A | 1/1993 | Bruemmer et al. |
| 5,192,606 A | 3/1993 | Proxmire et al. |
| 5,279,838 A | 1/1994 | McNeff |
| 5,306,487 A | 4/1994 | Karapasha et al. |
| 5,364,382 A | 11/1994 | Latimer et al. |
| 5,482,765 A | 1/1996 | Bradley et al. |
| 5,486,166 A | 1/1996 | Bishop et al. |
| 5,490,846 A | 2/1996 | Ellis et al. |
| 5,507,250 A | 4/1996 | Reddy et al. |
| 5,509,915 A | 4/1996 | Hansen et al. |
| 5,518,750 A | 5/1996 | Mcneff |
| 5,525,346 A | 6/1996 | Hartung et al. |
| 5,650,157 A | 7/1997 | Bockow |
| 5,723,149 A | 3/1998 | Bonte et al. |
| 5,730,965 A | 3/1998 | Rapaport |
| 5,797,891 A | 8/1998 | Wiersma |
| 5,800,818 A | 9/1998 | Prugnaud et al. |
| 5,843,056 A | 12/1998 | Good et al. |
| 5,860,391 A | 1/1999 | Maxwell et al. |
| 5,879,341 A | 3/1999 | Odorzynski et al. |
| 5,906,825 A | 5/1999 | Seabrook, Jr. et al. |
| 5,932,495 A | 8/1999 | Boney et al. |
| 5,957,906 A | 9/1999 | Roe et al. |
| 6,057,372 A | 5/2000 | Nobuhiro et al. |
| 6,063,382 A | 5/2000 | Nakajima et al. |
| 6,159,487 A | 12/2000 | Znaiden et al. |
| 6,228,265 B1 | 5/2001 | Henderson |
| 6,309,675 B1 | 10/2001 | Sobczak |
| 6,309,736 B1 | 10/2001 | McCormack et al. |
| 6,338,855 B1 | 1/2002 | Albacarys et al. |
| 6,485,734 B1 | 11/2002 | Baker et al. |
| 6,552,171 B2 * | 4/2003 | Howard et al. ............ 530/377 |
| 6,589,892 B1 | 7/2003 | Smith et al. |
| 6,686,303 B1 | 2/2004 | Haynes et al. |
| 2002/0119173 A1 | 8/2002 | Lin et al. |
| 2002/0120242 A1 | 8/2002 | Tyrrell et al. |
| 2002/0136755 A1 | 9/2002 | Tyrell et al. |
| 2003/0035785 A1 | 2/2003 | Palumbo et al. |
| 2003/0077307 A1 | 4/2003 | Klofta et al. |
| 2003/0105445 A1 | 6/2003 | Lange et al. |
| 2003/0118475 A1 | 6/2003 | Koenig et al. |
| 2003/0120228 A1 | 6/2003 | Koenig et al. |

FOREIGN PATENT DOCUMENTS

| | | |
|---|---|---|
| DE | 100 01 712 A1 | 12/2000 |
| EP | 0 604 769 A2 | 7/1994 |

(Continued)

OTHER PUBLICATIONS

Yucca Schidigera, http://www.alibaba.com/catalog/10862654/Yucca_Extract_Powder_NP.html.*

(Continued)

*Primary Examiner*—Tatyana Zalukaeva
*Assistant Examiner*—Melanie J Hand
(74) *Attorney, Agent, or Firm*—Armstrong Teasdale LLP

(57) ABSTRACT

Wet wipes comprising a pathogen selective antimicrobial agent and an optional broad spectrum antimicrobial agent are disclosed. The pathogen selective antimicrobial agent is a *Yucca* species extract. The optional broad spectrum antimicrobial agent may be a synthetic broad spectrum antimicrobial agent, or a natural broad spectrum antimicrobial agent such as a botanical extract.

30 Claims, No Drawings

FOREIGN PATENT DOCUMENTS

| | | |
|---|---|---|
| EP | 0 614 597 A1 | 9/1994 |
| EP | 0 565 266 B1 | 1/1999 |
| EP | 0 776 760 B1 | 5/1999 |
| EP | 0 922 457 A1 | 6/1999 |
| JP | 61-291503 A | 12/1986 |
| JP | 61 291503 A | 12/1986 |
| JP | 4016163 A2 | 1/1992 |
| JP | 4074105 A2 | 3/1992 |
| JP | 7 107923 | 4/1995 |
| JP | 7149608 A2 | 6/1995 |
| JP | 8019595 A2 | 1/1996 |
| JP | 8119872 A2 | 5/1996 |
| JP | 9187229 A2 | 7/1997 |
| JP | 9328410 A2 | 12/1997 |
| JP | 10045566 A2 | 2/1998 |
| JP | 11147818 A | 6/1999 |
| JP | 11200245 A2 | 7/1999 |
| JP | 11 322630 | 11/1999 |
| JP | 11322630 | 11/1999 |
| JP | 11322630 A2 | 11/1999 |
| JP | 2000-169320 | 6/2000 |
| JP | 2001 011496 | 1/2001 |
| JP | 2001011496 | 1/2001 |
| JP | 2001-039812 A | 2/2001 |
| JP | 2002 285472 | 10/2002 |
| JP | 2002285472 | 10/2002 |
| KR | 218093 | 10/1999 |
| KR | 2002 090 740 | 12/2002 |
| WO | WO 96/41528 A1 | 12/1996 |
| WO | WO 99/20258 A1 | 4/1999 |
| WO | WO 00/64502 | 11/2000 |
| WO | WO 01/95726 A1 | 12/2001 |
| WO | WO 02/51358 A2 | 7/2002 |
| WO | WO 02/51456 A2 | 7/2002 |

OTHER PUBLICATIONS

Facey et al., Investigation of Plants Used in Jamaican Folk Medicine for Anti-Bacterial Activity, J. Pharm. Pharmacol., (1999), pp. 1455-1460, vol. 51:12.

Farrington, E., Diaper Dermatitis, Pediatr. Nurs. (1992), pp. 81-82, vol. 18.

Fiers, S. A., Breaking the Cycle: The Etiology of Incontinence Dermatitis and Evaluating and Using Skin Care Products, Ostomy/Wound Management, The Journal for Extended Patient Care Management, (1996), pp. 32-43, vol. 42:3, USA.

Gnan, S.O. et al., Inhibition of *Staphylococcus aureus* by aueous Goiaba Extracts, Journal of Ethnopharmacology, (1999), pp. 103-108, vol. 68.

Janniger, C.K. et al., Diaper Dermatitis: An Approach to Prevention Employing Effective Diaper Care, Cutis, (1993), pp. 153-155, vol. 52.

Li, X.-C. et al., Antifungal Jujubogenin Saponins from Colubrina Retusa, J. Nat. Prod., (1999), pp. 674-677, vol. 62:5.

Lowe et al., The Ameliorating Effect of *Yucca schidigera* Extract on Canine and Feline Faecal Aroma, Res Vet Sci, (1997), pp. 61-66, vol. 63:1, Gilbertson and Page Ltd., Welwyn Garden City, USA, PMID 9368958, UI 98035433 (Abstract).

Lowe et al., The Effect of *Yucca schidigera* Extract on Canine and Feline Faecal Volatiles Occurring Concurrently with Faecal Aroma Amelioration, Res Vet Sci, (1997), pp. 67-71, vol. 63:1, Gilbertson and Page Ltd., Welwyn Garden City, USA, PMID 9368959, UI 98035434 (Abstract).

Miyakoshi, M. et al., Antiyeast Steroidal Saponins from *Yucca schidigera* (Mohave Yucca), A New Anti-Food-Deteriorating Agent, J. Nat. Prod., (2000), pp. 332-338, vol. 63:3.

Nostro, A. et al., Extraction Methods and Bioautography for Evaluation of Medicinal Plant Antimicrobial Activity, Letters in Applied Microbiology, (2000), pp. 379-384, vol. 30.

Papadopoulou, K. et al., Compromised Disease Resistance in Saponin-Deficient Plants, Proceedings of the National Academy of Sciences of the U.S.A., (1999), pp. 12923-12928, vol. 96:22.

Sen et al., Effect of Quillaja Saponaria Saponins and *Yucca schidigera* Plant Extract on Growth of *Escherichia coli*, Lett Appl Microbiol, (1998), pp. 35-38, vol. 27:1, Institute for Animal Production in the Tropics and Subtropics, University of Hohenheim, Stuttgart, Germany, PMID 9722995, UI 98390235 (Abstract).

Sires, U.I. et al., Diaper Dermatitis, How to Treat and Prevent, Postgraduate Medicine, (1995), pp. 79-84, vol. 98:6.

Tanako, et al., Application of Saponins in Foods and Cosmetics: Saponins of Mohave Yucca and Sapindus Mukurossi, Adv Exp Med Biol, (1996), pp. 1-11, vol. 405, Suzugamine Women's College, Hiroshima, Japan, PMID 8910691, UI 97067277 (Abstract).

Wallace, et al., Influence of *Yucca shidigera* Extract on Ruminal Ammonia Concentrations and Ruminal Microorganisms, Appl Environ Microbiol, (1994), pp. 1762-1767, vol. 60:6, Rowett Research Institute, Bucksburn, Aberdeen, United Kingdom, PMID 8031077, UI 94304158 (Abstract).

Van Setten et al., Molecular Structures of Saponins from *Quillaja saponaria* Molina, Adv. Exp. Med. Biol., (1996), pp. 185-193, vol. 404.

Wong, D.L. et al., Diapering Choices: A Critical Review of the Issues, Pediatric Nursing, (1992), pp. 41-54, vol. 18:1.

Yeo, et al., Effect of Feeding Diets Containing an Antibiotic, a Probiotic, or Yucca Extract on Growth and Intestinal Urease Activity in Broiler Chicks, Poult Sci, (997), pp. 381-385, vol. 76:2, Department of Animal Science, Cheju National University, Republic of Korea, PMID 9057222, UI 97210047 (Abstract).

*Yucca schidigera*, Printout from Geocites Website.

PCT International Search Report for International Application No. PCT/US 02/34952 dated Feb. 24, 2003.

PCT International Search Report for International Application No. PCT/US 02/34951 dated Mar. 6, 2003.

International Search Report from PCT/US2004/011043 dated Nov. 4, 2004.

Guangyao, "Effects of Yucca Extract on Environmental Pollution from Piggeries and on Growth Performance of Pigs," *Forestry Production and Chemical Engineering Bulletin*, (2000) vol. 14, No. 2, (English translation).

Tegos, et al., "Multidrug pump inhibitors uncover remarkable activity of plant antimicrobials," Antimicrobial Agents and Chemotherapy, Research Support, U.S. Gov't, P.H.S., Oct. 2002, Medline AN=NLM12234835.

Office action from European Application No. 04 749 945.4, dated Jun. 4, 2007.

\* cited by examiner

WIPE COMPRISING A PATHOGEN SELECTIVE ANTIMICROBIAL

CROSS REFERENCE TO RELATED APPLICATION

This application is a continuation-in-part patent application of U.S. patent application Ser. No. 10/029,404 filed on Dec. 20, 2001, which is incorporated in its entirety.

BACKGROUND OF THE INVENTION

The present invention relates generally to wipes, such as wet wipes, and more particularly to a wet wipe comprising a pathogen selective antimicrobial. More specifically, the present invention relates to wet wipes comprising a combination of a pathogen selective antimicrobial and a trace amount of a synthetic or natural broad spectrum antimicrobial. Various methods of improving skin health are also included within the scope of the present invention.

Diaper rash is caused by several factors, one of which is prolonged exposure to moisture. Moisture is conducive to bacteria growth and promotes skin maceration and breakdown which allows the bacteria to infect the damaged skin. The occasional presence of feces, which can include vast numbers of organisms, further increases the potential for bacterial and fungal infection of damaged skin. Further, some bacteria produce ammonia through degradation of urine. Ammonia is used as a nutritional substrate by bacteria, resulting in growth of more bacteria and production of more ammonia in an increasing detrimental cycle. The production of ammonia also raises the pH of the skin. Normal skin pH is between about 4 and about 6.8. This range tends to inhibit bacterial growth. As pH increases, bacterial growth increases. Further, some enzymes contained in feces such as lipases and proteases which damage skin are more active at high pH. The skin can also be damaged by an increase in pH. Thus, the production of ammonia causes several detrimental effects which can lead to diaper rash.

Increases in ammonia also increase offensive odors which can be embarrassing, particularly for incontinent adults. Thus, reduction of ammonia production from urine is advantageous for several reasons, including improving skin health and decreasing unwanted odors. Accordingly, there is a need for a wipe or other preparation which reduces production of ammonia.

As noted above, the proliferation of some types of bacteria on the skin's surface can lead to unwanted problems associated with the skin. Although most bacteria located on or near the surface of skin are potentially detrimental, such as Gram negative bacteria (and yeast), some bacteria, including some Gram positive bacteria, are actually beneficial on the skin surface. As such, it would be beneficial to have a wet wipe product for cleaning skin that comprises a pathogen selective antimicrobial which could substantially minimize or eliminate the growth of Gram negative bacteria and yeast yet not substantially affect the growth of Gram positive bacteria. Additionally, it would be beneficial to have a wet wipe comprising a pathogen selective antimicrobial in combination with a trace amount of a broad spectrum antimicrobial to substantially or completely eliminate potentially harmful bacteria from the skin's surface.

SUMMARY OF THE INVENTION

Briefly, the present invention includes a wet wipe for improving skin health. The wet wipe comprises a wipe substrate and a liquid formulation. The liquid formulation comprises a pathogen selective antimicrobial *Yucca* species extract capable of controlling the growth of Gram negative bacteria and yeast.

The present invention also includes a wet wipe for improving skin health comprising a wipe substrate and a liquid formulation. The liquid formulation comprises a pathogen selective antimicrobial *Yucca* species extract and a broad spectrum antimicrobial.

Additionally, the present invention includes a method for improving skin health. The method comprises contacting the skin with a wet wipe capable of reducing the growth rate of Gram negative bacteria and yeast on the surface of skin while not substantially affecting the growth rate of Gram positive bacteria. The wet wipe comprises a wipe substrate and a liquid formulation. The liquid formulation comprises a *Yucca* species extract.

The present invention also includes a method for improving skin health. The method comprises contacting the skin with a wet wipe capable of reducing the growth rate of Gram negative bacteria and yeast on the surface of skin while not substantially affecting the growth rate of Gram positive bacteria. The wet wipe comprises a wipe substrate and a liquid formulation. The liquid formulation comprises a *Yucca* species extract and a broad spectrum antimicrobial.

Other features of the present invention will be in part apparent and in part pointed out hereinafter.

DETAILED DESCRIPTION OF THE PREFERRED EMBODIMENT

In accordance with the present invention, it has been discovered that compositions containing a *Yucca* species extract, and more particularly *Yucca schidigera* are highly effective urease inhibitors (i.e., substances which inhibit production of ammonia from urine) when the compositions are applied directly to the skin or incorporated into a substrate such as a woven or non-woven material and used as a wipe. Additionally, it has been discovered that *Yucca* species extracts are pathogen selective antimicrobial agents that can be incorporated directly into a wet wipe solution, soap, or lotion alone, or in combination with a trace amount of a natural, broad spectrum antimicrobial to control bacterial growth.

The compositions of the present invention can be incorporated into a wet wipe, hand wipe, household wipe, industrial wipe and the like having an improved ability to inhibit production of ammonia from urine. Materials suitable for the substrate of the wet wipe described herein are well known to those skilled in the art, and are typically made from a fibrous sheet material which may be either woven or nonwoven. For example, the wet wipes incorporating the ammonia inhibiting compositions of the present invention may include nonwoven fibrous sheet materials which include meltblown, coformed, air-laid, bonded-carded web materials, hydroentangled materials, and combinations thereof. Such materials can comprise synthetic or natural fibers, or a combination thereof. Typically, wet wipes have a basis weight of between about 25 grams per square meter and about 120 grams per square meter and desirably between about 40 grams per square meter and about 90 grams per square meter.

In one embodiment, the wet wipes incorporating the ammonia inhibiting compositions of the present invention comprise a flexible sheet such as a coformed basesheet of polymeric microfibers and cellulosic fibers having a basis weight between about 60 grams per square meter and about 80 grams per square meter and desirably about 75 grams per square meter. Such coformed basesheets are manufactured generally as described in U.S. Pat. No. 4,100,324, which is hereby incorporated by reference. Typically, such coformed basesheets comprise a gas-formed matrix of thermoplastic polymeric meltblown microfibers (e.g., polypropylene microfibers) and cellulosic fibers (e.g., wood pulp fibers).

The relative percentages of the polymeric microfibers and cellulosic fibers in the coformed basesheet can vary over a wide range depending upon the desired characteristics of the wet wipes. For example, the coformed basesheet may comprise between about 20 weight percent and about 100 weight percent, desirably between about 20 weight percent and about 60 weight percent, and more desirably between about 30 weight percent and about 40 weight percent of the polymeric microfibers based on the dry weight of the coformed basesheet being used to provide the wet wipes.

Alternatively, the wet wipes incorporating the ammonia inhibiting compositions of the present invention may comprise a flexible sheet such as a composite including multiple layers of materials. For example, the wet wipes may include a three layer composite including an elastomeric film or meltblown layer between two coformed layers as described above. In such a configuration, the coformed layers may define a basis weight between about 15 grams per square meter and about 30 grams per square meter and the elastomeric layer may include a film material such as a polyethylene metallocene film.

As mentioned above, one type of wipe suitable for use in combination with the additives described herein to improve skin health include wet wipes, which contain a liquid solution or formulation. The liquid can be any solution, which can be absorbed into the wet wipe basesheet and may include any suitable components, which provide the desired wiping properties. For example, the components may include water, emollients, surfactants, fragrances, preservatives, chelating agents, pH buffers, or combinations thereof as are well known to those skilled in the art. Further, the liquid may also contain lotions, and medicaments.

Each wet wipe is generally rectangular in shape and may have any suitable unfolded width and length. For example, the wet wipe may have an unfolded length of from about 2.0 to about 80.0 centimeters and desirably from about 10.0 to about 25.0 centimeters and an unfolded width of from about 2.0 to about 80.0 centimeters and desirably from about 10.0 to about 25.0 centimeters. Typically, each individual wet wipe is arranged in a folded configuration and stacked one on top of the other to provide a stack of wet wipes. Such folded configurations are well known to those skilled in the art and include c-folded, z-folded, quarter-folded configurations and the like. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

As previously mentioned, in one embodiment described herein the wet wipes contain a urease inhibiting composition which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe contains between about 150 weight percent and about 600 weight percent and desirably between about 250 weight percent and about 450 weight percent solution based on the dry weight of the wipe for improved wiping.

In one particular embodiment, in which the wet wipes are made from a coformed material comprising between about 30 weight percent and about 40 weight percent polymeric microfibers based on the dry weight of the wipe, the amount of solution contained within the wet wipe is between about 300 weight percent and about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

The urease inhibiting solution incorporated into the wet wipes should contain an amount of *Yucca* species extract sufficient to provide urease inhibiting activity. A suitable amount of *Yucca* species extract is at least about 0.001 weight percent, and more desirably at least about 0.01 weight percent based on the total weight of the solution. Further, the amount of *Yucca* species extract should be small enough to prevent undesirable coloration of the solution. Desirably, the amount of *Yucca* species extract is less than about 1.0 weight percent based on total weight of the solution. Although other *Yucca* species extracts may be used without departing from the scope of the present invention, in one embodiment the *Yucca* species extract comprises *Yucca schidigera*, and more particularly, a *Yucca schidigera* solution sold under the trade designation Yucca 70 by Sher-Mar Enterprises of Poway, Calif.

The urease inhibiting solution of the present invention which is incorporated into the wet wipes may also contain a variety of other components which may assist in providing the desired wiping and urease inhibiting properties. For example, the components may include water, emollients, other surfactants, preservatives, chelating agents, pH buffers, fragrances, urease inhibiting actives, or combinations or mixtures thereof. The solution may also contain lotions and/or medicaments. To provide reduced skin irritation, the solution desirably includes at least about 80 weight percent water and more desirably at least about 90 weight percent water based on the total weight of the solution.

In another embodiment of the present invention, the compositions can be incorporated into products to be directly applied to the skin. Such products may include hand and body lotions as well as various types of soaps. The urease inhibiting lotion or soaps should contain an amount of *Yucca* species extract sufficient to provide urease inhibiting activity. A suitable amount of *Yucca* species extract for incorporation into lotions is at least about 0.001 weight percent, and more desirably at least about 0.01 weight percent based on the total weight of the lotion. Further, the amount of *Yucca* species extract should be small enough to prevent undesirable coloration of the lotion. Desirably, the amount of *Yucca* species extract is less than about 1.0 weight percent based on total weight of the lotion. Although other species extracts may be used without departing from the scope of the present invention, in one embodiment the *Yucca* species extract comprises *Yucca schidigera*, and more particularly, a *Yucca schidigera* solution sold under the trade designation Yucca 70 by Sher-Mar Enterprises.

For soaps, a suitable amount of *Yucca* species extract is at least about 0.001 weight percent, and more desirably at least about 0.01 weight percent based on the total weight of the soap. Further, the amount of *Yucca* species extract should be small enough to prevent undesirable coloration of the soap. Desirably, the amount of *Yucca* species extract is less than about 1.0 weight percent based on total weight of the soap.

Although other *Yucca* species extracts may be used without departing from the scope of the present invention, in one embodiment the *Yucca* species extract comprises *Yucca schidigera*, and more particularly, a *Yucca schidigera* solution sold under the trade designation Yucca 70 by Sher-Mar Enterprises.

The urease inhibiting soaps and lotions of the present invention may also contain a variety of other components which may assist in providing the desired cleaning and urease inhibiting properties. For example, the soaps or lotions may also contain an alcohol such as ethyl alcohol, isopropyl alcohol, propyl alcohol, or mixtures of ethyl and isopropyl alcohols. Also, the lotions and soaps may contain water, emollients, other surfactants, preservatives, chelating agents, pH buffers, fragrances, urease inhibiting actives, or combinations or mixtures thereof. Typically, the lotions and soaps will contain a high percentage of water to reduce the possibility of skin irritation.

In another embodiment, the urease inhibiting compositions of the present invention incorporating a urease inhibiting agent can be incorporated into or onto a cellulosic web substrate such as facial tissue, bathroom tissue, feminine care product, hand towels, surgical drapes, gowns, bedsheets, pillowcases and the like. In this embodiment, the substrate will typically contain at least about 0.001 weight percent, and more desirably at least about 0.01 weight percent based on the dry weight of the substrate. Further, the amount of *Yucca* species extract should be small enough to prevent undesirable coloration of the substrate. Desirably, the amount of *Yucca* species extract is less than about 1.0 weight percent based on total weight of the substrate. Although other *Yucca* species extracts may be used without departing from the scope of the present invention, in one embodiment the *Yucca* species extract comprises *Yucca schidigera*, and more particularly, a *Yucca schidigera* solution sold under the trade designation Yucca 70 by Sher-Mar Enterprises. It is envisioned that the composition may be applied to at least one of the outer faces of the sheet by a conventional process such as printing or coating. Alternatively, the composition may be held within the sheet between its outer faces.

As will be appreciated by those skilled in the art, the previously described urease inhibiting compositions may be used to inhibit production of ammonia from urine such as occurs when urine is held adjacent a user's skin by an article such as a diaper, training pants, other child care products, other infant care products, adult care products and feminine care products. The compositions are applied to an area of the wearer's skin. As will be appreciated by those skilled in the art, the compositions may applied to the skin by any conventional method such as being applied directly to the skin as a lotion or indirectly applied to the skin during use of a product (e.g., as a residue of soap or from a wipe). Although the compositions may be applied in other concentrations without departing from the scope of the present invention, in one embodiment at least about 0.001 gram per square centimeter of *Yucca* species extract is applied to the area of the user's skin.

In another embodiment of the present invention, a *Yucca* species extract can be introduced into a wet wipe solution, hand and/or body lotion, or soap such that the *Yucca* species extract acts as a pathogen selective antimicrobial agent when the wet wipe solution is contacted with the skin. *Yucca* species extracts such as Yucca 70 liquid, 100% *Yucca Schidigera* powder, and 50% Food Grade Yucca, when contacted with bacteria and yeast, act as pathogen selective antimicrobial agents; that is, the *Yucca* species extract will substantially minimize or eliminate the growth or kill certain types of bacteria and yeast, while not substantially affecting the growth of other types of bacteria and yeast.

The *Yucca* species extracts, when introduced into a wet wipe solution, for example, are effective in significantly reducing or eliminating the growth of Gram negative bacteria and yeasts such as *E. coli* and *Candida albicans*. Although the *Yucca* species extracts are capable of reducing the growth of these problem bacteria and yeast, they do not substantially inhibit the growth of beneficial, naturally occurring Gram positive bacteria such as *Staphlococcus epidermidis*. As such, when a wet wipe comprising a *Yucca* species extract contacts the skin, the growth of potentially harmful Gram negative bacteria and yeast on the skin's surface can be substantially reduced or eliminated without significantly affecting the growth of beneficial Gram positive bacteria. This provides an important skin health benefit.

When introduced into a wet wipe solution for use as a pathogen selective antimicrobial agent, the *Yucca* species extracts are typically introduced in an amount of from about 0.0001% (by total weight of the formulation) to about 5% (by total weight of the formulation), and desirably from about 0.01% (by total weight of the formulation) to about 1% (by total weight of the formulation). It will be recognized based on the disclosure herein by one skilled in the art that the exact amount of *Yucca* species extract introduced into the wet wipe solution will depend, in part, upon the intended use for the wet wipes.

In an alternative embodiment of the present invention, a pathogen selective antimicrobial *Yucca* species extract can be introduced into the wet wipe solution in combination with a broad spectrum antimicrobial agent. As used herein, the term "broad spectrum antimicrobial agent" is meant to include antimicrobial agents that are substantially equally effective in inhibiting the growth of, or killing, Gram negative bacteria, Gram positive bacteria, and yeast. In this embodiment, the broad spectrum antimicrobial agent is a supplement to the pathogen selective *Yucca* species antimicrobial agent and is typically introduced into the wet wipe solution in only a trace amount; that is, in such an amount that would not be sufficient to kill all of the bacteria present on the skin if the broad spectrum antimicrobial were used alone and without the pathogen selective antimicrobial agent in the wet wipe solution. Because the pathogen selective antimicrobial *Yucca* species extracts do not always completely inhibit the growth of, or kill, all of the Gram negative bacteria and yeast present on the skin, by introducing a trace amount of broad spectrum antimicrobial agent into the wet wipe solution, the combination of antimicrobial agents will substantially inhibit the growth of, or kill, the problematic bacteria and yeast, while only having a slightly negative impact on the beneficial flora due to the broad spectrum antimicrobial agent. After application to the skin of the wet wipe formulation, the skin is left cleaned and with beneficial flora on the surface thereof.

The broad spectrum antimicrobial agent can be any broad spectrum antimicrobial agent suitable for use in a wet wipe system for use on the skin which is substantially non-antagonistic to the other components of the wet wipe solution. The broad spectrum antimicrobial agent can be a synthetic antimicrobial agent, or can be a naturally occurring antimicrobial agent. In a preferred embodiment, the broad spectrum antimicrobial agent is a natural broad spectrum antimicrobial agent, such as a botanical extract, herb or essential oil.

The broad spectrum antimicrobial agent is typically introduced into the wet wipe solution in only a trace amount as noted above. If too much broad spectrum antimicrobial agent is introduced into the wet wipe solution, the solution will inhibit the growth of, or kill, all of the bacteria and yeast on the skin's surface and the pathogen selective *Yucca* species extract will be of no benefit with regard to the flora as all of the flora will have been eliminated. If not enough broad spectrum antimicrobial agent is introduced into the wet wipe solution, a small amount of Gram negative bacteria and yeast may survive the antimicrobial treatment of the skin's surface and continue to be a potential problem. It is desirable that a sufficient amount of broad spectrum antimicrobial agent be introduced into the wet wipe solution so as to act as a supplement to the pathogen selective *Yucca* species extract. The broad spectrum antimicrobial agent should be added in an amount sufficient to kill or substantially inhibit the growth of substantially all of the Gram negative bacteria and yeast that the *Yucca* species extract does not kill or inhibit the growth of. Although some beneficial Gram positive bacteria may also be eliminated by the broad spectrum antimicrobial agent, the overall affect is positive on the skin's surface as the combination of pathogen selective antimicrobial agent and broad spectrum antimicrobial agent leaves the skin clean and with beneficial flora thereon.

Specifically, the amount of broad spectrum antimicrobial agent introduced into the wet wipe solution is typically from about 0.0001% (by total weight of the formulation) to about 0.1% (by total weight of the formulation), and desirably from about 0.0001% (by total weight of the formulation) to about 0.01% (by total weight of the formulation). Within these ranges, the broad spectrum antimicrobial agent can perform its intended supplementary function.

Suitable synthetic-type broad spectrum antimicrobial agents include, for example, alcohols having from one to about 6 or 7 carbon atoms per molecule. Alcohols exhibit antimicrobial properties when used at sufficiently high concentrations and/or with viscosity increasing agents (e.g., thickeners) to increase the residence time of the alcohol on the skin or on a surface where the alcohol is delivered. Other suitable synthetic-type broad spectrum antimicrobial agents include triclosan (2,4,4'-trichloro-2'-hydroxydiphenyl ether), triclocarban, p-chloro-m-xylenol, benzalkonium chloride, chlorohexidine gluconate, hexachlorophene and the like, and combinations thereof.

Suitable natural broad spectrum antimicrobial agents include, for example, aloe vera, folic acid, calendula flower, *echinacea purpurea* tops, gota kola extract, chlorophyll, phytoplenolin extract, chamomile flower, blood root, prickly ash bark, green tea leaf, oregano leaf, peppermint oil, cinnamon bark, eucalyptus leaf, lavender oil, bio-saponin concentrate, olive leaf extract, black walnut green hulls, clove leaf, thyme herb, grapefruit seed extract, vegetable glycerin, and combinations thereof.

In order to enhance consumer appeal for the wet wipes, additional ingredients can be added to the above-described wet wipe formulations including the pathogen selective *Yucca* species extract and broad spectrum antimicrobial agent. Suitable additional ingredients include, for example, anti-acne actives, antifoaming agents, antifungal actives, antiseptic actives, antioxidants which prevent oxidation during processing and storage by preferentially oxidizing to preserve the antioxidency of the antioxidant agent described herein, astringents, colorants, deodorants, film formers, fragrances, moisturizers, chelating agents, skin protectants, sunscreen actives, and solvents.

The present invention is illustrated by the following examples which are merely for the purpose of illustration and is not to be regarded as limiting the scope of the invention or manner in which it may be practiced.

EXAMPLE 1

Various commercially available *Yucca* species extracts used for animal feed supplements were tested to determine their urease inhibiting efficacy. Two milliliters (ml) of the respective *Yucca* species extract, 18 ml of urine and 2 ml of jack bean urease (10 milligrams/milliliter (mg/ml)) were placed in a 50 ml conical tube. The jack bean urease was obtained from Sigma Chemical Company of St. Louis, Mo., and identified as U-4002. The final concentration of jack bean urease used was 0.91 mg/ml (1.0 mg jack bean urease=1000 U). The tube was capped and the contents vigorously mixed with a vortex. After a two hour incubation period at 25 degrees Celsius, the ammonia in gas phase above the mixture was analyzed using a Gastec® ammonia detection tube available from Gastec Corporation of Ayase-shi Kanagawa-ken, Japan. A control mixture containing 2 ml of de-ionized water, 18 ml of urine and 2 ml of jack bean urease was also analyzed.

Four *Yucca* species extracts which were tested included 100% pure *Yucca schidigera* powder sold under the trade designation Desert Pure Yucca by Sher-Mar Enterprises of Poway, Calif., a *Yucca schidigera* solution sold under the trade designation Yucca 70 by Sher-Mar Enterprises, 50% food grade yucca powder sold under the product code YUCEXT50 by Garuda International, Inc. of Lemon Cove, Calif., and a yucca powder sold under the trade designation Dinase-30-dry by Diversified Nutri-Agri Technologies, Inc. of Gainesville, Ga. The Desert Pure Yucca and the Dinase-30-dry yucca powders exhibited low apparent urease inhibiting activity. The 50% food grade yucca exhibited medium apparent urease inhibiting activity, and the Yucca 70 exhibited high apparent urease inhibiting activity. Specific results are shown in Table 1.

TABLE 1

| Yucca Extract | Extract Concentration | Ammonia Measured (ppm) | % Inhibition of Released Ammonia |
| --- | --- | --- | --- |
| None | — | 780 | — |
| Dinase-30-dry | 0.9 mg/ml | 620 | 20.5 |
| Yucca 70 | 9.1% | 130 | 83.3 |
| 100% pure *Yucca schidigera* powder | 0.9 mg/ml | 740 | 5.1 |
| 50% food grade yucca powder | 0.5 mg/ml | 600 | 23.1 |

EXAMPLE 2

Various concentrations of *Yucca schidigera* extract were studied to determine their urease inhibiting efficacy. An amount of a *Yucca schidigera* solution sold under the trade designation Yucca 70 by Sher-Mar Enterprises was thoroughly mixed in a vortex with 18 ml of urine and 2 ml of jack bean urease. After a 2 hour incubation period at 25 degrees Celsius, the resulting mixture was analyzed with an ammonia detection tube. A control mixture containing only 18 ml of urine, 2 ml of de-ionized water and 2 ml of jack bean urease was also analyzed.

The results of the mixtures containing the Yucca species extract were compared to the control mixture. The final concentrations of the *Yucca* species extract analyzed were zero weight percent per volume (control mixture), 0.9 percent, 4.6 percent, and 9.1 percent. The 0.9 percent mixture containing 6.3 milligrams of *Yucca* species extract solids per milliliter of urine demonstrated about 54 percent reduction in gas phase ammonia from the control mixture. The 4.6 percent mixture containing 31.5 milligrams of Yucca species extract solids per milliliter of urine and the 9.1 percent mixture containing 63 milligrams of *Yucca* species extract solids per milliliter of urine demonstrated more than 90 percent reduction in gas phase ammonia from the control mixture. Specific results are shown in Table 2.

TABLE 2

| Yucca-70 Concentration (%) | Ammonia Measured (ppm) | % Inhibition of Released Ammonia |
|---|---|---|
| 0 | 610 | — |
| 0.9 | 283 | 53.6 |
| 4.6 | 38 | 93.8 |
| 9.1 | 53 | 91.3 |

EXAMPLE 3

This Example is similar to Example 2 except that *Proteus mirabilis* was used instead of jack bean urease. Various concentrations of *Yucca schidigera* extract were studied to determine their efficacy for inhibiting this type of urease.

*Proteus mirabilis* (ATCC 29906) bacteria were recovered from frozen state by growing the appropriate bacterial coated MicroBank Bead (available from Pro Lab, Inc. of Austin, Tex.) in 10 ml of trypticase soy broth (TSB) (available from Difco of Ann Arbor, Mich.) in a 15 ml sterile loosely tightened screw capped conical tube overnight at 37 degrees Celsius. The tube was held stationary. Upon observation of turbidity, the bacterial suspension was checked for purity by isolation plate and Gram stain. Once determined that the isolate was *Proteus mirabilis*, a colony from the isolation plate was transferred to 10 ml of TSB in a 15 ml sterile screw capped conical tube and incubated overnight at 37 degrees Celsius under facultative conditions. Bacterial suspension from this overnight TSB culture was used.

An amount of a *Yucca schidigera* solution sold under the trade designation Yucca 70 by Sher-Mar Enterprises was thoroughly mixed in a vortex with 18 ml of urine and 2 ml of *Proteus mirabilis* prepared as described above. After a 22 hour incubation period at 37 degrees Celsius, the resulting mixture was analyzed with an ammonia detection tube and pH paper (available from Sigma Chemical Company of St. Louis, Mo.). A control mixture containing only 18 ml of urine, 2 ml of de-ionized water and 2 ml of *Proteus mirabilis* was also analyzed.

The results of the mixtures containing the *Yucca* species extract were compared to the control mixture. The final concentrations of the *Yucca* species extract analyzed were zero weight percent per volume (control mixture), 0.9 percent, 4.6 percent, and 9.1 percent. The 0.9 percent mixture containing 6.3 milligrams of *Yucca* species extract solids per milliliter of urine demonstrated substantially no reduction in gas phase ammonia from the control mixture and a pH about the same as the pH of the control mixture, i.e., 9.2. The 4.6 percent mixture containing 31.5 milligrams of *Yucca* species extract solids per milliliter of urine demonstrated about 60 percent reduction in gas phase ammonia from the control mixture and a pH of about 8.8, and the 9.1 percent mixture containing 63 milligrams of *Yucca* species extract solids per milliliter of urine demonstrated more than 90 percent reduction in gas phase ammonia from the control mixture and a pH of about 7.5. Specific results are shown in Table 3.

TABLE 3

| Yucca-70 Concentration (%) | Ammonia Measured (ppm) | % Inhibition of Released Ammonia |
|---|---|---|
| 0 | 710 | — |
| 0.9 | 850 | no effect |
| 4.6 | 285 | 59.9 |
| 9.1 | 52 | 92.7 |

EXAMPLE 4

In this Example, three different *Yucca* species extracts were evaluated for their ability to selectively inhibit the growth of five different bacteria and one yeast.

The *Yucca* species extracts evaluated were 100% pure *Yucca Schidigera* powder sold under the trade designation Desert Pure Yucca by Sher-Mar Enterprises (Poway, Calif.), a *Yucca Schidigera* solution sold under the trade designation Yucca 70 by Sher-Mar Enterprises, and 50% food grade Yucca powder sold under the product code YUCEXT50 by Garuda International, Inc. (Lemon Cove, Calif.). The five bacteria evaluated were *Escherichia coli, Staphylococcus epidermidis, Proteus mirabilis, Staphlococcus aureus*, and *Corynebacterium ammoniagenes* The yeast evaluated was *Candida albicans*.

Cultures:

*Proteus mirabilis* (ATCC 29906) bacteria, *Escherichia coli* (ATCC 8739) bacteria, *Staphylococcus epidermidis* (ATCC 12228), *Staphlococcus aureus* and *Cornebacterium ammoniagenes* bacteria were separately recovered from frozen state by growing the appropriate bacterial coated MicroBank Bead (Pro Lab, Inc., Austin Tex.) in 10 mL of trypitcase soy broth (TSB) (Difco, Ann Arbor, Mich.) in a 50 mL sterile loosely tightened screw capped conical tube overnight at 37° C. The tube was shaken at between about 125 and about 150 rpm. Upon observation of turbidity, the bacterial suspension was checked for purity by isolation plate and Gram stain. Once determined that the isolate was the appropriate bacteria, a colony from the isolation plate was transferred to 10 mL of TSB in a 50 mL sterile screw capped conical tube and incubated overnight at 37° C. The tube was shaken at between about 125 and about 150 rpm. Bacterial suspension from this overnight TSB culture was used for testing. *Candida albicans* was similarly recovered using a Sabourads broth (SAB).

Growth Inhibition Assay:

Each of the *Yucca* species extracts was tested at eight different concentrations: (1) 0%; (2) 0.0003%; (3) 0.0016%; (4) 0.008%; (5) 0.04%; (6) 0.2%; (7) 1.0%; and (8) 5.0%. Each sample was prepared in TSB or SAB as appropriate. The final volume of each well was 100 microliters. The following samples were prepared for each *Yucca* species extract:

1. 10%: 100 µl or 100 mg Yucca+900 µl or 1000 µl SAB or TSB
2. 5.0%: 75 µl of 10%+75 µl SAB or TSB
3. 1.0%: 25 µl of 5%+100 µl SAB or TSB
4. 0.2%: 25 µl of 1% solution+100 µl SAB or TSB
5. 0.04%: 25 µl of 0.2% solution+100 µl SAB or TSB
6. 0.008%: 25 µl of 0.04% solution+100 µl SAB or TSB
7. 0.0016%: 25 µl of 0.008 solution+100 µl SAB or TSB
8. 0.0003%: 25 µl of 0.0016 solution+100 µl SAB or TSB
9. 0%: 100 µl TSB or SAB.

To each sample was added 50 µl of *Candida albicans* culture in SAB at about $1 \times 10^6$ cells/ml or a 1:200 dilution of bacteria culture in TSB and an optical density reading at 650 nanometers was taken. After the reading, the samples were incubated for about 16 hours at 37° C. at about 400 rpm. After incubation, a second optical density reading was taken at 650 nanometers. From the optical density readings, the results were calculated as follows:

$$OD_{650} = OD_{650 \text{ at } 16 \text{ hours}} - OD_{650 \text{ at } 0 \text{ hours}}$$

The Optical Density at 650 nm results for *Candida albicans* are shown in Table 4:

TABLE 4

| Yucca Extract | 5.0% | 1.0% | 0.2% | 0.04% | 0.008% | 0.0016% | 0.0003% | 0% |
|---|---|---|---|---|---|---|---|---|
| Yucca 70 | −0.120 | −0.041 | −0.021 | −0.006 | 0.983 | 0.972 | 0.966 | 1.074 |
| 100% Pure *Yucca Schidigera* Powder | 0.005 | 0.037 | 0.003 | 0.018 | 1.023 | 1.005 | 0.990 | 1.074 |
| 50% Food Grade Yucca Powder | 0.015 | 0.002 | 0.008 | 0.967 | 1.025 | 1.010 | 1.004 | 1.074 |

The Optical Density at 650 nm results for *Escherichia coli* are shown in Table 5:

TABLE 5

| Yucca Extract | 5.0% | 1.0% | 0.2% | 0.04% | 0.008% | 0.0016% | 0.0003% | 0% |
|---|---|---|---|---|---|---|---|---|
| Yucca 70 | 0.195 | 0.310 | 0.455 | 0.506 | 0.516 | 0.545 | 0.488 | 0.634 |
| 100% Pure *Yucca Schidigera* Powder | 0.370 | 0.401 | 0.439 | 0.382 | 0.525 | 0.536 | 0.458 | 0.634 |
| 50% Food Grade Yucca Powder | 0.532 | 0.790 | 0.651 | 0.529 | 0.747 | 0.604 | 0.605 | 0.634 |

The Optical Density at 650 nm results for *Proteus mirabilis* are shown in Table 6:

TABLE 6

| Yucca Extract | 5.0% | 1.0% | 0.2% | 0.04% | 0.008% | 0.0016% | 0.0003% | 0% |
|---|---|---|---|---|---|---|---|---|
| Yucca 70 | 0.301 | 1.063 | 0.987 | 1.050 | 1.032 | 1.067 | 1.070 | 1.104 |
| 100% Pure *Yucca Schidigera* Powder | 0.458 | 1.068 | 0.966 | 0.993 | 1.084 | 1.057 | 1.072 | 1.104 |
| 50% Food Grade Yucca Powder | 0.758 | 1.016 | 0.964 | 0.968 | 1.062 | 1.056 | 1.055 | 1.104 |

The Optical Density at 650 nm results for *Staphlococcus epidermidis* are shown in Table 7:

TABLE 7

| Yucca Extract | 5.0% | 1.0% | 0.2% | 0.04% | 0.008% | 0.0016% | 0.0003% | 0% |
|---|---|---|---|---|---|---|---|---|
| Yucca 70 | 0.414 | 0.527 | 0.227 | 0.358 | 0.470 | 0.454 | 0.472 | 0.485 |
| 100% Pure *Yucca Schidigera* Powder | 0.364 | 0.373 | 0.372 | 0.423 | 0.335 | 0.328 | 0.383 | 0.485 |
| 50% Food Grade Yucca Powder | 0.439 | 0.581 | 0.500 | 0.379 | 0.395 | 0.360 | 0.430 | 0.485 |

The Optical Density at 650 nm results for *Staphlococcus aureus* are shown in Table 8:

TABLE 8

| Yucca Extract | 5.0% | 1.0% | 0.2% | 0.04% | 0.008% | 0.0016% | 0.0003% | 0% |
|---|---|---|---|---|---|---|---|---|
| Yucca 70 | 0.255 | 0.51 | 0.40 | 0.573 | 0.486 | 0.468 | 0.654 | 0.970 |
| 100% Pure *Yucca Schidigera* Powder | −0.059 | 0.72 | 0.73 | 0.746 | 0.504 | 0.49 | 0.535 | 0.97 |
| 50% Food Grade Yucca Powder | 0.106 | 0.514 | 0.66 | 0.556 | 0.49 | 0.474 | 0.53 | 0.97 |

The Optical Density at 650 nm results for *Corynebacterium ammoniagenes* are shown in Table 9:

TABLE 9

| Yucca Extract | 5.0% | 1.0% | 0.2% | 0.04% | 0.008% | 0.0016% | 0.0003% | 0% |
|---|---|---|---|---|---|---|---|---|
| Yucca 70 | −0.222 | 0.266 | 0.276 | 0.175 | 0.229 | 0.21 | 0.208 | 0.272 |
| 100% Pure *Yucca Schidigera* Powder | 0.038 | 0.074 | 0.11 | 0.198 | 0.214 | 0.233 | 0.201 | 0.072 |
| 50% Food Grade Yucca Powder | 0.085 | 0.224 | 0.202 | 0.321 | 0.34 | 0.215 | 0.168 | 0.272 |

As the data in Tables 4-9 indicate, the Yucca species extracts generally showed high activity against Gram negative bacteria and yeast, while not substantially affecting the growth of Gram positive bacteria.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A wet wipe for improving skin health comprising a wipe substrate and a liquid formulation, the liquid formulation comprising a *Yucca* species extract and a broad spectrum antimicrobial.

2. The wet wipe as set forth in claim 1 wherein the *Yucca* species extract is selected from the group consisting of Yucca 70 liquid, 100% Yucca Schidigera powder, and 50% Food Grade Yucca powder.

3. The wet wipe as set forth in claim 1 wherein the liquid formulation comprises from about 0.0001% (by total weight of the formulation) to about 5% (by total weight of the formulation) *Yucca* species extract.

4. The wet wipe as set forth in claim 1 wherein the liquid formulation comprises from about 0.01% (by total weight of the formulation) to about 1% (by total weight of the formulation) *Yucca* species extract.

5. The wet wipe as set forth in claim 1 wherein the broad spectrum antimicrobial is a botanical extract.

6. The wet wipe as set forth in claim 1 wherein the broad spectrum antimicrobial is selected from the group consisting of alcohols having from one to about 6 or 7 carbon atoms per molecule, triclosan, triclocarban, p-chloro-m-xylenol, benzalkonium chloride, chlorohexidine gluconate, hexachlorophene, and combinations thereof.

7. The wet wipe as set forth in claim 1 wherein the broad spectrum antimicrobial is present in the liquid formulation in an amount of from about 0.0001% (by total weight of the formulation) to about 0.1% (by total weight of the formulation).

8. The wet wipe as set forth in claim 1 wherein the broad spectrum antimicrobial is present in the liquid formulation in an amount of from about 0.0001% (by total weight of the formulation) to about 0.01% (by total weight of the formulation).

9. The wet wipe as set forth in claim 1 further comprising an additional component selected from the group consisting of anti-acne actives, antifoaming agents, antifungal actives, antiseptic actives, antioxidants astringents, colorants, deodorants, film formers, fragrances, moisturizers, chelating agents, skin protectants, sunscreen actives, solvents, and combinations thereof.

10. A wet wipe for improving skin health comprising a wipe substrate and a liquid formulation, the liquid formulation comprising a *Yucca* species extract and a natural broad spectrum antimicrobial.

11. The wet wipe as set forth in claim 10 wherein the *Yucca* species extract is selected from the group consisting of Yucca 70 liquid, 100% Yucca Schidigera powder, and 50% Food Grade Yucca powder.

12. The wet wipe as set forth in claim 10 wherein the liquid formulation comprises from about 0.0001% (by total weight of the formulation) to about 5% (by total weight of the formulation) *Yucca* species extract.

13. The wet wipe as set forth in claim 10 wherein the liquid formulation comprises from about 0.01% (by total weight of the formulation) to about 1% (by total weight of the formulation) *Yucca* species extract.

14. The wet wipe as set forth in claim 10 wherein the natural broad spectrum antimicrobial is a botanical extract.

15. The wet wipe as set forth in claim 10 wherein the natural broad spectrum antimicrobial is selected from the group consisting of aloe vera, folic acid, calendula flower, echinacea purpurea tops, gota kola extract, chlorophyll, phytoplenolin extract, chamomile flower, blood root, prickly ash bark, green tea leaf, oregano leaf, peppermint oil, cinnamon bark, eucalyptus leaf, lavender oil, bio-saponin concentrate, olive leaf extract, black walnut green hulls, clove leaf, thyme herb, grapefruit seed extract, vegetable glycerin, and combinations thereof.

16. The wet wipe as set forth in claim 10 wherein the natural broad spectrum antimicrobial is present in the liquid formulation in an amount of from about 0.0001% (by total weight of the formulation) to about 0.1% (by total weight of the formulation).

17. The wet wipe as set forth in claim 10 wherein the natural broad spectrum antimicrobial is present in the liquid formulation in an amount of from about 0.0001% (by total weight of the formulation) to about 0.01% (by total weight of the formulation).

18. The wet wipe as set forth in claim 10 further comprising an additional component selected from the group consisting of anti-acne actives, antifoaming agents, antifungal actives, antiseptic actives, antioxidants astringents, colorants, deodorants, film formers, fragrances, moisturizers, chelating agents, skin protectants, sunscreen actives, solvents, and combinations thereof.

19. A method for improving skin health comprising contacting the skin with a wet wipe capable of reducing the growth rate of Gram negative bacteria and yeast on the surface of the skin while not substantially affecting the growth rate of Gram positive bacteria, the wet wipe comprising a wipe substrate and a liquid formulation, the liquid formulation comprising a *Yucca* species extract.

20. The method as set forth in claim 19 wherein the *Yucca* species extract is selected from the group consisting of Yucca 70 liquid, 100% Yucca Schidigera powder, and 50% Food Grade Yucca powder.

21. The method as set forth in claim 19 wherein the *Yucca* species extract is present in the formulation is an amount of from about 0.0001% (by total weight of the formulation) to about 5% (by total weight of the formulation).

22. The method as set forth in claim 19 wherein the Yucca extract is present in the formulation in an amount of from about 0.01% (by total weight of the formulation) to about 1% (by total weight of the formulation).

23. A method for improving skin health comprising contacting the skin with a wet wipe capable of reducing the growth rate of Gram negative bacteria and yeast on the surface of the skin while not substantially affecting the growth rate of Gram positive bacteria, the wet wipe comprising a wipe substrate and a liquid formulation, the liquid formulation comprising a *Yucca* species extract and a natural broad spectrum antimicrobial.

24. The method as set forth in claim 23 wherein the *Yucca* species extract is selected from the group consisting of Yucca 70 liquid, 100% Yucca Schidigera powder, and 50% Food Grade Yucca powder.

25. The method as set forth in claim 23 wherein the liquid formulation comprises from about 0.0001% (by total weight of the formulation) to about 5% (by total weight of the formulation) *Yucca* species extract.

26. The method as set forth in claim 23 wherein the liquid formulation comprises from about 0.01% (by total weight of the formulation) to about 1% (by total weight of the formulation) *Yucca* species extract.

27. The method as set forth in claim 23 wherein the natural broad spectrum antimicrobial is a botanical extract.

28. The method as set forth in claim 23 wherein the natural broad spectrum antimicrobial is selected from the group consisting of aloe vera, folic acid, calendula flower, echinacea purpurea tops, gota kola extract, chlorophyll, phytoplenolin extract, chamomile flower, blood root, prickly ash bark, green tea leaf, oregano leaf, peppermint oil, cinnamon bark, eucalyptus leaf, lavender oil, bio-saponin concentrate, olive leaf extract, black walnut green hulls, clove leaf, thyme herb, grapefruit seed extract, vegetable glycerin, and combinations thereof.

29. The method as set forth in claim 23 wherein the natural broad spectrum antimicrobial is present in the liquid formulation in an amount of from about 0.0001% (by total weight of the formulation) to about 0.1% (by total weight of the formulation).

30. The method as set forth in claim 23 wherein the natural broad spectrum antimicrobial is present in the liquid formulation in an amount of from about 0.0001% (by total weight of the formulation) to about 0.01% (by total weight of the formulation).

* * * * *

UNITED STATES PATENT AND TRADEMARK OFFICE
CERTIFICATE OF CORRECTION

| | | |
|---|---|---|
| PATENT NO. | : 7,485,110 B2 | Page 1 of 1 |
| APPLICATION NO. | : 10/608661 | |
| DATED | : February 3, 2009 | |
| INVENTOR(S) | : Koenig et al. | |

It is certified that error appears in the above-identified patent and that said Letters Patent is hereby corrected as shown below:

In the Specification, column 6, line 10, delete "Staphlococcus epidermidis" and insert therefor -- Staphylococcus epidermidis --.

In the Specification, column 10, line 27, delete "Staphlococcus aureus" and insert therefor -- Staphylococcus aureus --.

In the Specification, column 11, above Table 7, delete "Staphlococcus epidermidis" and insert therefor -- Staphylococcus epidermidis --.

In the Specification, column 11, above Table 8, delete "Staphlococcus aureus" and insert therefor -- Staphylococcus aureus --.

Signed and Sealed this

Thirtieth Day of June, 2009

JOHN DOLL
*Acting Director of the United States Patent and Trademark Office*